United States Patent [19]
Nordman et al.

[11] Patent Number: 5,993,743
[45] Date of Patent: *Nov. 30, 1999

[54] HAND-HELD VEHICLE EXHAUST ANALYZER

[75] Inventors: Jonathan D. Nordman, Owatonna; Timothy J. Wolf; John D. Neal, both of Blooming Prairie; Troy J. Liebl; Peter D. Johnson, both of Owatonna, all of Minn.

[73] Assignee: SPX Corporation, Muskegon, Mich.

[ * ] Notice: This patent issued on a continued prosecution application filed under 37 CFR 1.53(d), and is subject to the twenty year patent term provisions of 35 U.S.C. 154(a)(2).

[21] Appl. No.: 08/824,895

[22] Filed: Mar. 26, 1997

[51] Int. Cl.[6] .............................. G01N 7/18; G01N 33/22
[52] U.S. Cl. .............................. 422/94; 422/83; 422/98; 436/137; 436/177; 73/23.31; 73/23.32; 73/863.23; 356/437; 356/438; 356/439; 250/339.13; 250/343
[58] Field of Search .................................. 436/116, 134, 436/137, 139, 140, 141, 142, 143, 177; 422/82.05, 83, 94, 98; 73/23.31, 23.32, 863.23; 356/437, 438, 439; 250/339.13, 343

[56] References Cited

U.S. PATENT DOCUMENTS

| | | | |
|---|---|---|---|
| 3,276,241 | 10/1966 | Hubner | 422/83 |
| 3,593,023 | 7/1971 | Dodson | 436/134 |
| 3,864,964 | 2/1975 | Voelz | 73/116 |
| 3,917,454 | 11/1975 | Clark | 436/116 |
| 3,942,157 | 3/1976 | Azure | 340/172.5 |
| 3,957,372 | 5/1976 | Jowett et al. | 356/51 |
| 4,117,914 | 10/1978 | Snyder | 190/58 R |
| 4,441,359 | 4/1984 | Ezoe | 73/117 |
| 4,457,161 | 7/1984 | Iwanaga et al. | 73/23 |
| 4,670,405 | 6/1987 | Stetter et al. | 436/151 |
| 4,678,914 | 7/1987 | Melrose et al. | 250/343 |
| 4,691,562 | 9/1987 | Abthoff et al. | 73/118.1 |
| 4,782,690 | 11/1988 | Terasaka | 73/116 |
| 4,786,472 | 11/1988 | McConnell et al. | 436/134 |
| 4,818,348 | 4/1989 | Stetter | 204/15 |
| 5,059,397 | 10/1991 | Melly et al. | 422/94 |
| 5,060,505 | 10/1991 | Tury et al. | 73/16 |
| 5,067,103 | 11/1991 | Lapeyre | 364/709.16 |
| 5,105,651 | 4/1992 | Gutmann | 73/23.31 |
| 5,218,347 | 6/1993 | Deppe | 340/634 |
| 5,319,199 | 6/1994 | Stedman et al. | 250/338.5 |
| 5,343,906 | 9/1994 | Tibbals, III | 141/83 |
| 5,426,934 | 6/1995 | Hunt et al. | 60/276 |
| 5,485,922 | 1/1996 | Butcher | 206/576 |
| 5,510,269 | 4/1996 | Black et al. | 436/164 |
| 5,550,375 | 8/1996 | Peters et al. | 250/343 |
| 5,731,510 | 3/1998 | Jones et al. | 73/23.31 |

*Primary Examiner*—Jill Warden
*Attorney, Agent, or Firm*—Kinney & Lange

[57] ABSTRACT

A vehicle gas analyzing system for testing gas content in exhaust emitted from a vehicle is disclosed. The vehicle gas analyzing system is of a size and weight to be held in a user's hands. The system includes a housing having outer dimensions no greater than about 12"×8"×3", and has an inlet receiving exhaust emitted from the vehicle. A sensor assembly is disposed in the housing, receives the exhaust emitted from the vehicle through the inlet, and determines the content of a plurality of different gases in the exhaust. A user interface is disposed on an outside surface of the housing, allowing a user to input instructions to the system and to perceive output from the system. A control system is disposed in the housing, is operatively coupled with the sensor assembly and the user interface, and is operable to receive and interpret instructions input by a user via the user interface, regulate operations of the sensor assembly in response to the instructions received, receive and interpret results of operations of the sensor assembly, and transmit the results as output to the user interface. A power supplying apparatus is disposed in the housing, receives power from an external source, and delivers power throughout the system. The housing, sensor assembly, user interface, control system, and power supplying apparatus have a combined weight of no greater than about five pounds.

8 Claims, 6 Drawing Sheets

5,993,743

HAND-HELD VEHICLE EXHAUST ANALYZER

BACKGROUND OF THE INVENTION

The present invention relates to a portable, hand-held vehicle gas analyzer.

Due to government regulations, testing of vehicle exhaust emissions for compliance with minimum standards has become a necessary function for testing facilities and repair garages. Originally, only hydrocarbons and carbon monoxide had to be measured, but stricter standards have added oxygen and carbon dioxide, and still stricter regulations require oxides of nitrogen to be measured as well for compliance with statutory requirements. If a vehicle fails an emission test, it must be repaired. In the repair process, a mechanic must be able to tell whether the repairs have affected the content of the exhaust gas that was at an unacceptable level during the emission test. Therefore, there is a need for a vehicle gas analyzer that can be used by repair technicians to determine whether their repairs have remedied emission test failures.

Large platform engine analyzers were initially developed to measure gases emitted in vehicle exhaust. These platform engine analyzers were large devices that were transported by wheeling them around on a large cart. These large engine analyzers are typically utilized by government agencies to perform actual emission tests on vehicles, but their size and considerable expense make them difficult for smaller repair garages to own.

"Portable" exhaust gas analyzers were subsequently developed to be used for repair purposes. While portable exhaust gas analyzers are smaller than the larger platform analyzers used previously, they still weigh over thirty pounds, and are too large to be held in the hands of a user during operation. The units contain a large heater, since the infrared sensing equipment in these units operates at a temperature greater than ambient temperature. Typically a chopper motor is employed to serve as a zero reference for infrared sensors operating in the analyzers. A large pump is also required to advance high volumes of exhaust gas through the analyzer. These components draw a large amount of power, compelling the implementation of a large power supply within the analyzer, take significant amounts of space, and generate substantial heat, necessitating the use of metal throughout the analyzer and reducing the analyzer's "portability". In addition, it is often difficult to remove and replace the parts of the analyzer, such as filters or the pump, which regularly wear out.

Therefore, there is a need for an improved portable exhaust gas analyzer, such as a hand-held vehicle gas analyzer, which is of a size and weight to be carried easily by a user, while still performing the same functions of sampling and sensing gas content in vehicle exhaust as previous exhaust gas analyzers.

SUMMARY OF THE INVENTION

The present invention is a vehicle gas analyzing system for testing gas content and exhaust emitted from a vehicle. The vehicle gas analyzing system is of a size and weight to be held in a user's hands. The system includes a housing having outer dimensions no greater than about 12 inches by 8 inches by 3 inches. The housing has an inlet for receiving exhaust emitted from the vehicle under test. A sensor assembly is disposed in the housing and receives the exhaust emitted from the vehicle through the inlet. The sensor assembly determines the content of a plurality of different gases in the exhaust emitted from the vehicle. A user interface is disposed on an outside surface of the housing, allowing a user to input instructions to the system and to perceive output from the system. A control system is disposed in the housing and is operatively coupled with the sensor assembly and the user interface. The control system receives and interprets instructions input by a user via the user interface. The control system also regulates operations of the sensor assembly and responds to the instructions received from the user interface. The control system receives and interprets results of operations of the sensor assembly, and transmits the results as output to the user interface. A power supplying apparatus is disposed in the housing, and receives power from a source located externally from the housing and delivers power throughout the vehicle gas analyzing system. The housing, sensor assembly, user interface, control system, and power supplying apparatus has a combined weight of no greater than about five pounds.

According to one aspect of the vehicle gas analyzing system, the sensor assembly functions at ambient temperature. A filter assembly receives the exhaust emitted from the vehicle through an inlet and outputs filtered exhaust. The sensor assembly comprises a sensing system operating on the filtered exhaust to determine the content of a plurality of gases in the filtered exhaust and a pump assembly advancing the filtered exhaust through the sensing system at a rate of less than about one liter per minute. The power supplying apparatus delivers no greater than about 8 watts of power to the sensor apparatus, the user interface, and the control system of the gas analyzing system. The filter assembly, components of the sensing system, and the pump assembly are readily removable and replaceable by a user.

Another aspect of the invention is a filtering system for use in a vehicle gas analyzing system. The filtering system includes means for receiving exhaust emitted from a vehicle under test once it enters the gas analyzing system. A filter assembly separates gas in the received exhaust from dirt and moisture in the received exhaust. A drain plug is disposed on the filter assembly, and traps dirt and moisture separated from the received exhaust within the filter assembly. Dirt and moisture remain within the filter at all angular orientation of the vehicle gas analyzing system until the drain plug is physically opened. The filtering system passes only the gas separated from the received exhaust through the filtering system.

DETAILED DESCRIPTION OF THE PREFERRED EMBODIMENTS

Figure 1:
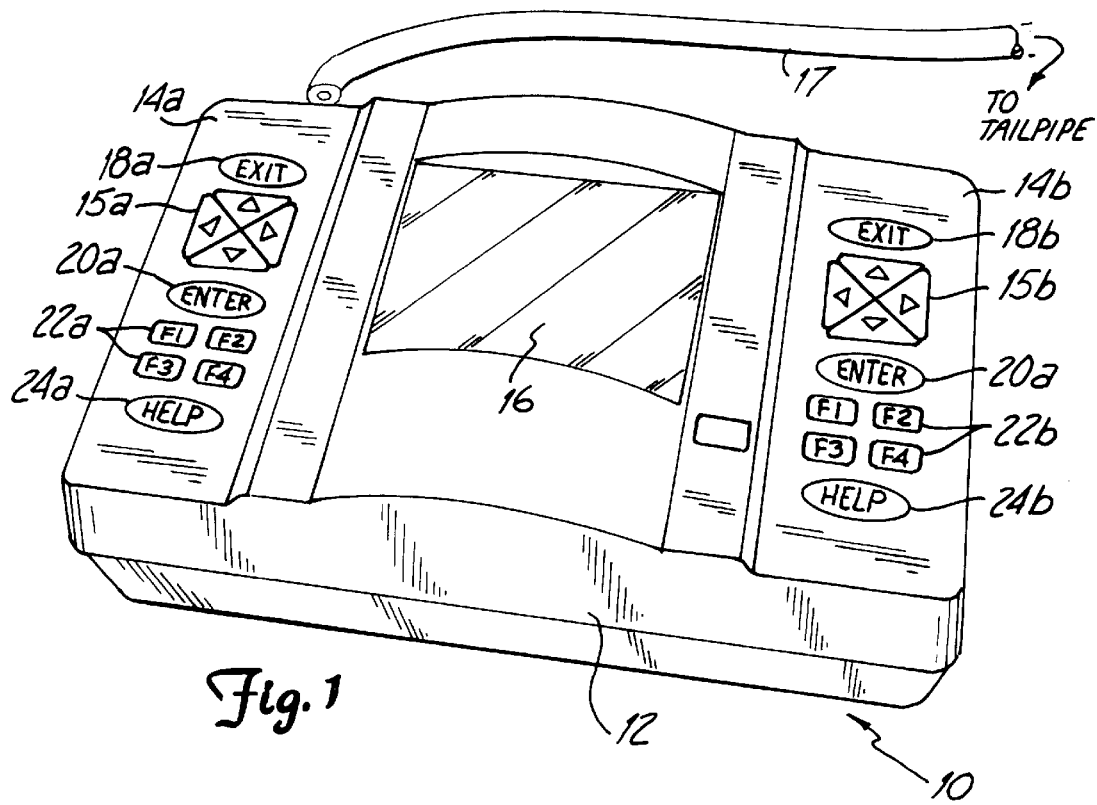
FIG. 1 is a front perspective view of the hand-held vehicle gas analyzer of the present invention.

FIG. 1 is a front perspective view of a portable, hand-held vehicle gas analyzer 10 according to the present invention.

Gas analyzer 10 has a housing 12, keyboards 14a and 14b, and display 16, and accepts exhaust gas samples from sample hose 17. Housing 12 is preferably composed of a polymeric material, in order to provide sufficient strength with minimal weight. Housing 12 is preferably about 12 inches by 8 inches, and about 3 inches thick, so that it can be easily held in the hands of a user. Keyboards 14a and 14b each include a number of keys, such as cursor control keys 15a and 15b, exit keys 18a and 18b, enter keys 20a and 20b, function keys 22a and 22b, and help keys 24a and 24b. The number of keys and the functions of keys may be varied according to design preferences. Display 16 is preferably a liquid crystal display (LCD). Display 16 may optionally be backlit, and in an alternative embodiment may accept tactile input from a finger or stylus. Sample hose 17 preferably has an inside diameter of about one-eighth of an inch.

Keyboards 14a and 14b and display 16 are disposed on a top surface of housing 12. In the embodiment shown in FIG. 1, keyboard 14a is positioned on the left side of display 16, and keyboard 14b is positioned on the right side of display 16, to accommodate both left- and right-handed users. In operation, a user enters commands and test parameters through keyboard 14a or 14b, and views instructions and exhaust gas analysis on display 16.

Figure 2:
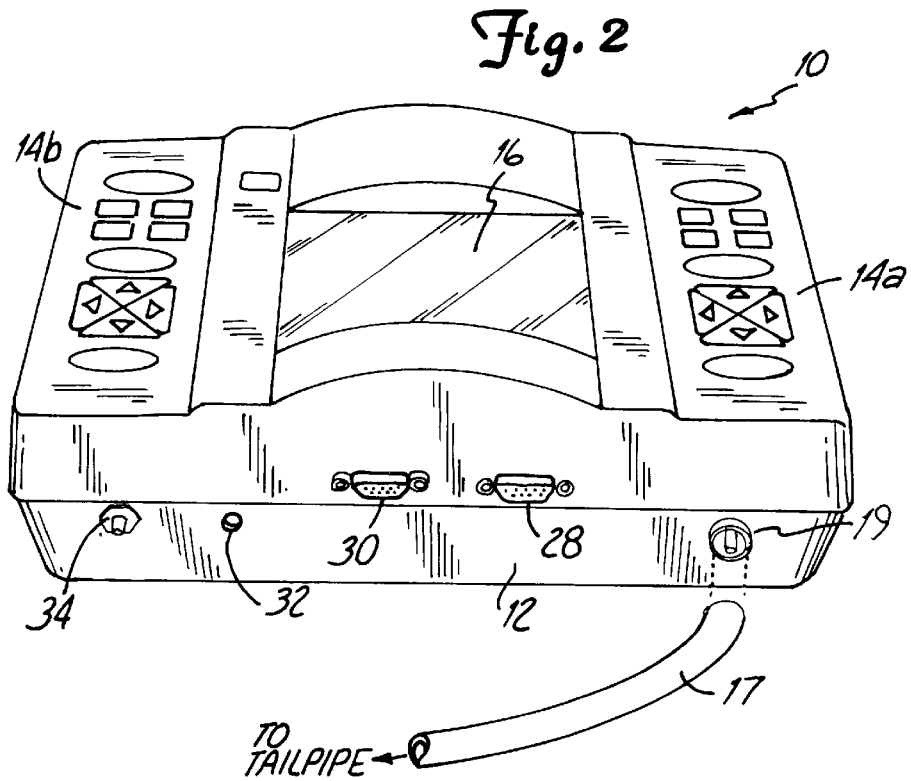
FIG. 2 is an rear perspective view of the hand-held vehicle gas analyzer shown in FIG. 1.

FIG. 2 is a back perspective view of the portable, hand-held vehicle gas analyzer 10 of the present invention. Gas analyzer 10 includes housing 12, keyboards 14a and 14b, and display 16, and accepts exhaust gas samples from sample hose 17. Housing 12 has a back surface which includes, arranged from right to left in FIG. 2, exhaust inlet nipple 19, DB9S connector 28, DB9P connector 30, power connector 32, and exhaust outlet 34. Alternatively, exhaust outlet 34 may be located on a side surface of housing 12.

Exhaust inlet nipple 19 makes a sealed connection to sample hose 17 so that exhaust gas from sample hose 17 may enter housing 12. DB9S connector 28 allows gas analyzer 10 to be connected to a personal computer (not shown). DB9P connector 30 allows gas analyzer 10 to be connected to an external printer or modem (not shown). Power connector 32 allows gas analyzer 10 to be connected to an external power source (not shown). Exhaust outlet 34 serves as an escape path for exhaust gas that has passed through housing 12.

Figure 3:
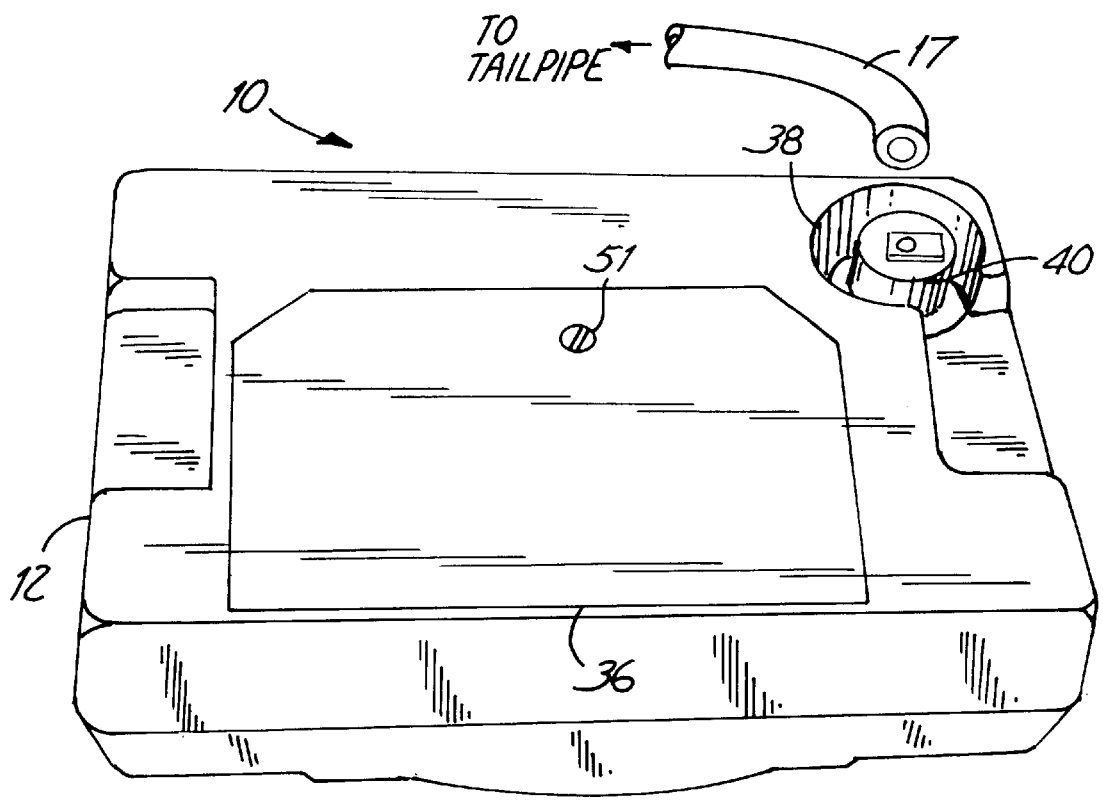
FIG. 3 is a bottom perspective view of the hand-held vehicle gas analyzer shown in FIG. 1.

FIG. 3 is a bottom view of the portable, hand-held vehicle gas analyzer 10 of the present invention. Gas analyzer 10 includes housing 12, which includes access panel 36 to cover a cavity in the housing that contains the internal components of the gas analyzer, and exhaust gas samples are input to the housing through sample hose 17. Housing 12 includes recessed hand grips 37 for ease of handling by a user, and also includes a recess 38 in which filter assembly 40 sits. Filter assembly 40 is shown in FIG. 6, and will be described in more detail later with reference to FIG. 6. The design of access panel 36 and recess 38 allows a user to easily access internal components and filter assembly 40 of the gas analyzer, so that parts may be easily accessed and replaced.

Figure 4:
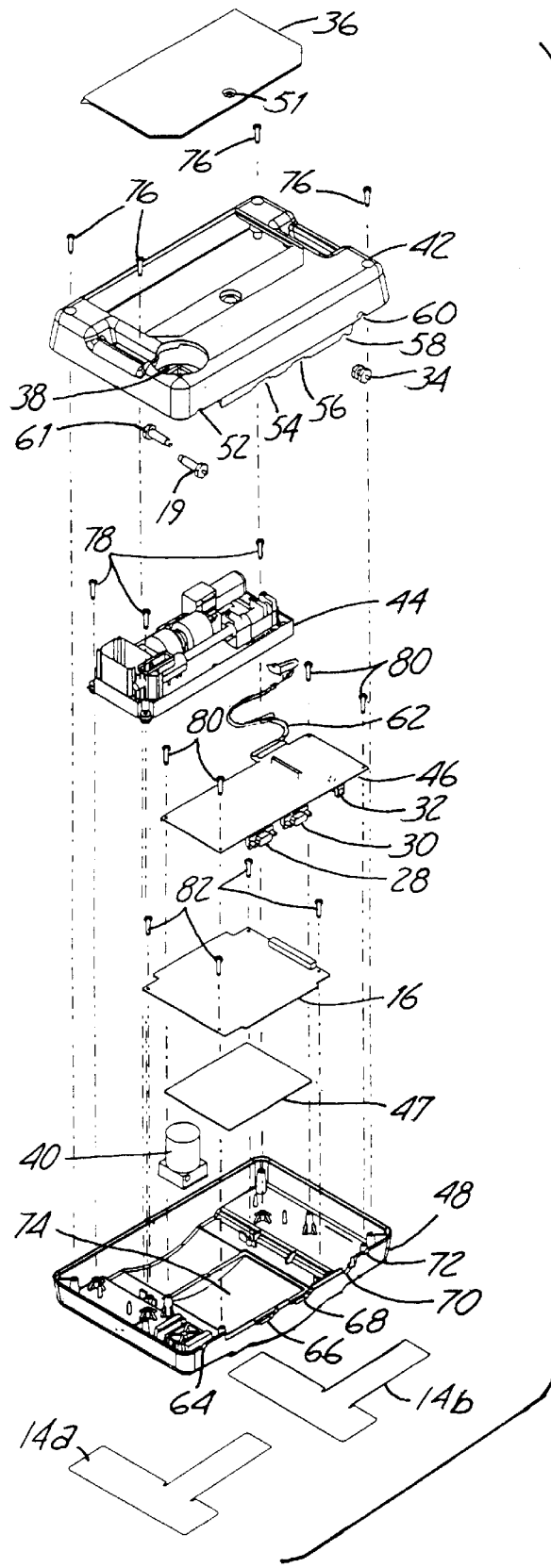
FIG. 4 is an exploded assembly diagram of the hand-held vehicle gas analyzer shown in FIG. 1.

FIG. 4 is an exploded assembly drawing of the portable, hand-held gas analyzer 10, which is inverted and shows the internal and external parts of the gas analyzer. Gas analyzer 10 includes, from top to bottom in FIG. 4, access panel 36, bottom housing 42, sensor assembly 44, controller printed circuit board (PCB) 46, display 16, lens 47, filter assembly 40, top housing 48, and keyboard membranes 14a and 14b.

Access panel 36 includes a quarter-turn connector 51 to provide for latching and unlatching of access panel 36, to open and close access to the inside of the housing. Bottom housing 42 includes notches 52, 54, 56, 58 and 60 to accommodate exhaust inlet 19, DB9S connector 28, DB9P connector 30, power connector 32, and exhaust outlet 34, respectively. Exhaust inlet nipple 19 provides a sealed path for exhaust to travel from a sample hose into the housing, and nipple fitting 61 provides a sealed path for exhaust to travel from filter assembly 40 to sensor assembly 44. Bottom housing 42 also includes recess 38 to allow access to filter assembly 40.

Figure 5:
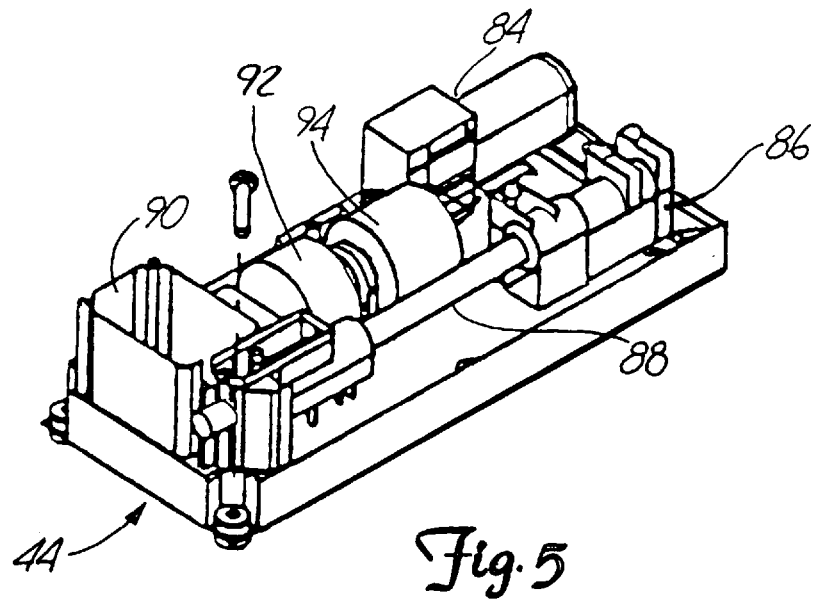
FIG. 5 is a perspective view showing the sensor assembly depicted in FIG. 4 in more detail.
Figure 7:
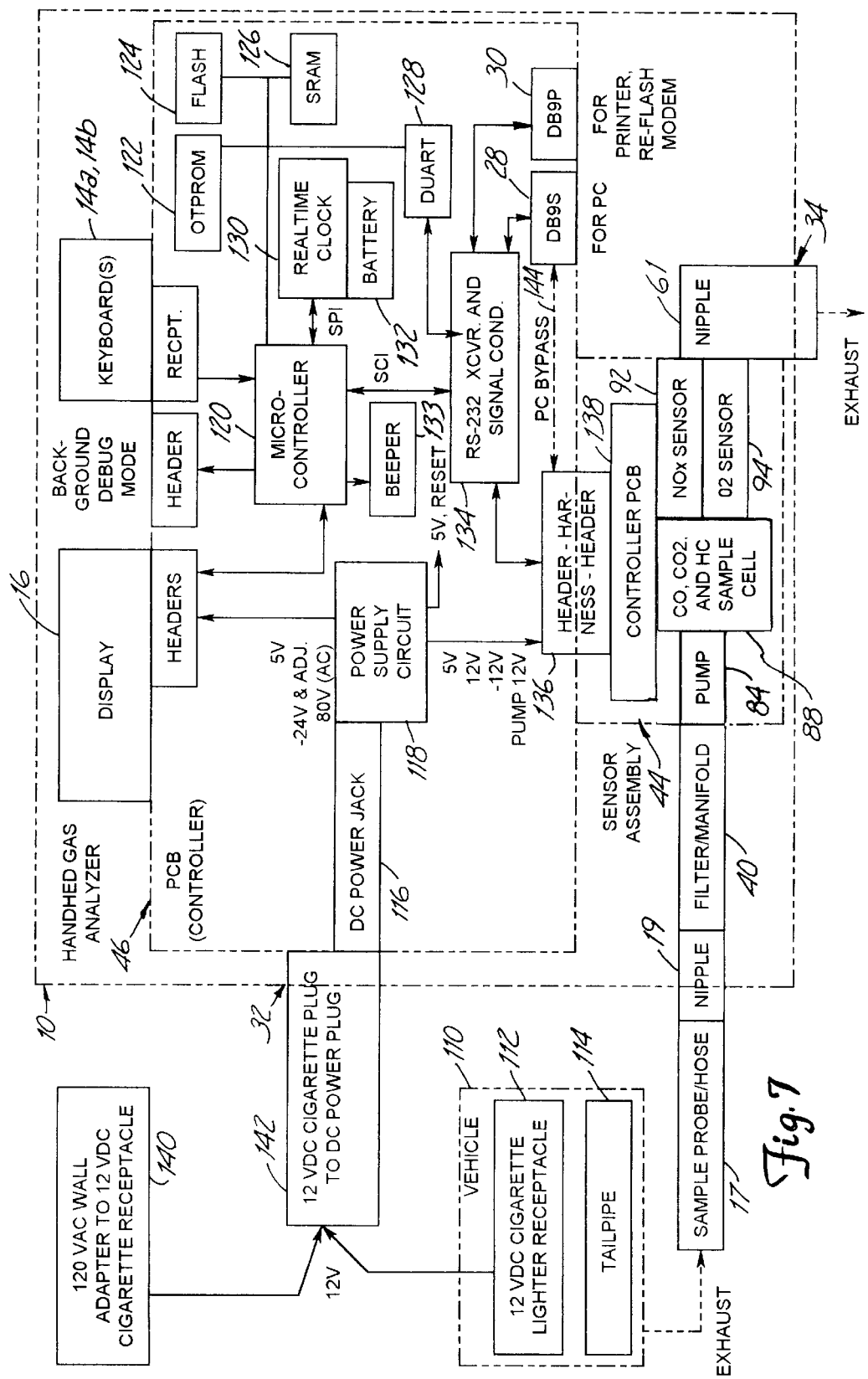
FIG. 7 is a block diagram of the functional elements of the hand-held vehicle gas analyzer shown in FIG. 1.

Sensor assembly 44 is shown in FIG. 5, and will be described in detail later with respect to FIG. 5. Controller PCB 46 includes a cable assembly 62 for connecting controller PCB to sensor assembly 44, and contains the control and power supply circuitry to operate gas analyzer 10. Controller PCB 46 has DB9S connector 28, DB9P connector 30, and power connector 32 mounted thereon. The functional components of controller PCB 46 are shown in FIG. 7, and will be discussed in more detail later with respect to FIG. 7.

Top housing 48 includes notches 64, 66, 68, 70 and 72 to accommodate exhaust inlet 19, DB9S connector 28, DB9P connector 30, power connector 32, and exhaust outlet 34, respectively. Top housing 48 also includes an aperture 74 through which display 16 can be viewed through lens 47.

Bottom housing 42 and top housing 48 are joined by screws 76 to form a housing to seal gas analyzer 10. Access panel 36, in its closed position, seals the internal components of the gas analyzer inside the housing. Sensor assembly 44 is mounted to top housing 48 by three screws 78. Sensor assembly 44 sits inside the housing of gas analyzer 10 directly adjacent access panel 36, so that the parts of sensor assembly 44 may be easily accessed and replaced by a user by simply opening access panel 36. Controller PCB 46 is mounted to top housing 48 by four screws 80, and is connected by cable assembly 62 to sensor assembly 44. Display 16 is mounted to top housing 48 by four screws 82. Lens 47 is positioned between display 16 and top housing 48, to protect display 16 and allow viewing of the display through lens 47. Filter assembly 40 is anchored to top housing 48, and sits in recess 38 in bottom housing 42 so that it may be easily accessed and replaced by a user. Keyboard membranes 14a and 14b are mounted on the outside of top housing 48, providing an interface for a user to input instructions to gas analyzer 10.

The entire hand-held gas analyzer 10, including all the components within the housing, has a weight of less than about five pounds, and the dimensions of the outer housing are preferably about 12 inches by 8 inches by 3 inches, so that the gas analyzer may be easily held in the hands of a user.

FIG. 5 is a perspective view showing in detail the parts of sensor assembly 44. Sensor assembly 44 may preferably be a gas bench such as Part No. 886600-000 manufactured by Andros, Inc., and includes pump assembly 84, infrared source 86, sample tube 88, optical block 90, nitrous oxide (NOx) sensor 92, and oxygen ($O_2$) sensor 94. Sensor assembly 44 must be designed to fit inside a cavity in the housing of the gas analyzer, underneath the access panel in the bottom of the housing.

In one embodiment, exhaust is received into sensor assembly 44 by pump assembly 84, which operates to deliver exhaust into sample tube 88. While the exhaust is in sample tube 88, infrared source 86 generates infrared light which travels through the exhaust in sample tube 88, and is reflected into optical block 90. The content of various gases (such as carbon monoxide, carbon dioxide, and hydrocarbons) can be determined by the response of different wavelengths of infrared light as they pass through the exhaust, as is known in the art. A zero reference is provided by a separate beam of infrared light, so that a chopper motor to repeatedly block the infrared sensing beam for a zero reference is not required. Exhaust then passes into NOx sensor 92 and $O_2$ sensor 94, which are chemical sensors operable to determine the content of the respective gases in the exhaust. In this way, the content of five gases (as required in many government emissions programs) in exhaust emitted from a vehicle is determined. Exhaust then exits sensor assembly 44 and is eventually released from gas analyzer 10 through exhaust outlet 34.

Sensor assembly 44 has a weight such that the weight of the entire gas analyzer 10 does not exceed about five pounds. Sensor assembly 44 preferably operates at ambient temperature, so that the housing of the gas analyzer can be composed of a polymeric material, which could not withstand high temperatures caused by a heater in the sensor assembly. Sensor assembly 44 is also designed to draw a small amount of power (preferably about 6 watts), so as not to require a large power supply which would destroy the portability of the gas analyzer 10. Prior gas analyzers required a heater to take thermally stable gas readings, which necessitated a large power supply and metal construction. The absence of a heater in gas analyzer 10 allows the housing to be composed of a polymeric material, reduces the overall size and weight of gas analyzer 10, and reduces the total power required by gas analyzer 10, so that the power supply need only deliver about 8 watts of total power. Sensor assembly 44 preferably has a sample rate of less than about one liter per minute, so that a sample hose with as small as one-eighth of an inch inner diameter may be used, and a low power pump assembly may be used.

Parts of the sensor assembly such as the sample tube 88, nitrous oxide sensor 92, oxygen sensor 94 and pump assembly 84 can be easily replaced by a user, by accessing the sensor assembly 44 through access panel 36 on the bottom of the housing 12. These parts are easily detachable from the sensor assembly 44, and may be individually removed and replaced.

Figure 6A:
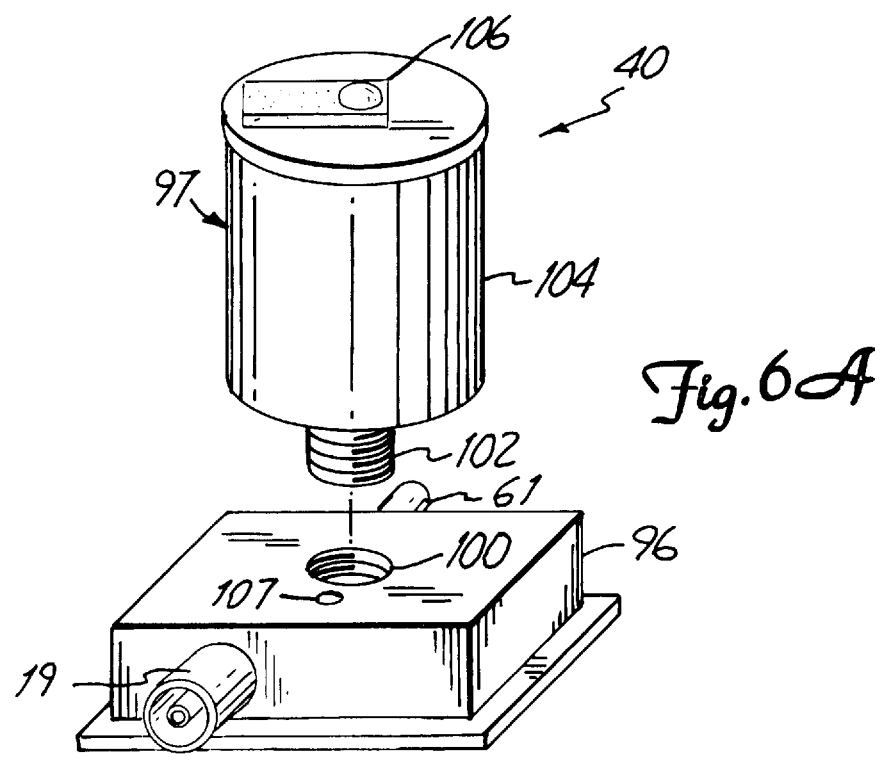
FIG. 6 is a perspective view showing the filter assembly depicted in FIG. 4 in more detail.
Figure 6B:
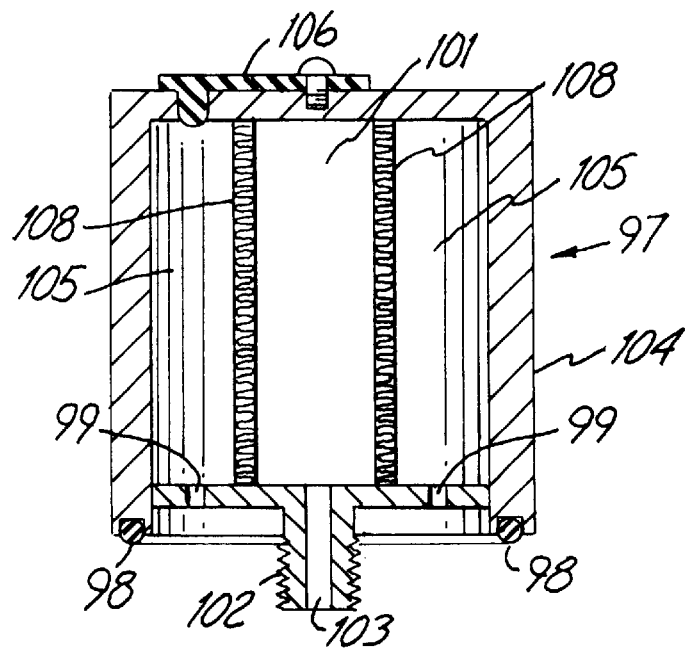
Figure 6C:
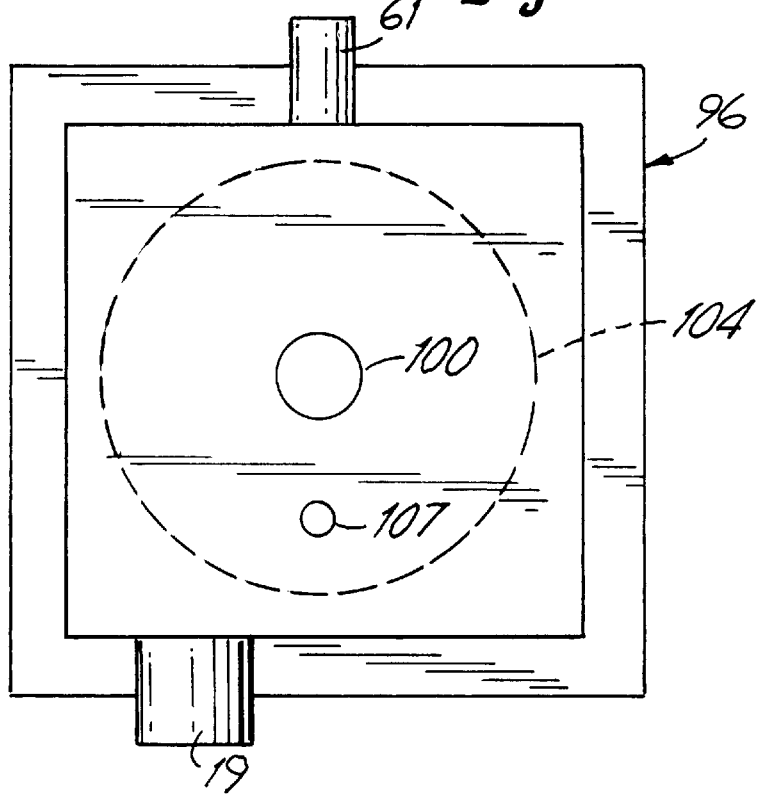

FIG. 6A shows a detailed perspective view of filter assembly 40, showing the filter unscrewed from the filter manifold, FIG. 6B shows a cross-sectional view of the filter, and FIG. 6C shows a top view of the filter manifold. Filter assembly 40 includes manifold 96 and filter 97. Manifold 96 includes inlet fitting nipple 19, outlet hole 107, threaded inlet hole 100, and outlet nipple fitting 61. Filter 97 includes threaded inlet 102, filter body 104, inner inlet holes 99, outer chamber 105, inner chamber 101, hydrophilic filter 108, and drain plug 106. Threaded inlet 102 includes passage 103 therethrough. Filter 97 attaches to filter manifold 96 by engaging threaded inlet 102 into manifold hole 100, and outer O-ring 98 of filter 97 seals against manifold 96, so that outlet hole 107 is inside outer O-ring 98. Drain plug 106 is provided to allow the filter to be emptied by a user when desired.

In operation, exhaust enters manifold 96 through inlet fitting nipple 19. The exhaust travels through the labyrinth inside manifold 96, up through outlet hole 107 in manifold 96, and into filter 97 inside outer O-ring 98. Manifold 96, since it is made of metal, provides a cold point to condense moisture out of the exhaust. Once exhaust enters filter 97 inside outer O-ring 98, it courses through the gap area in filter 97 and passes into outer chamber 105 through inner inlet holes 99. While any number of inner inlet holes 99 may be provided, four is a preferred number. The exhaust then circulates through filter 108 into central chamber 101. Filter 108 is preferably a hydrophilic membrane operating to remove both dirt and moisture from the exhaust. The filtered exhaust proceeds through passage 103 in threaded inlet 102 back into manifold 96, and is outlet from manifold 96 through outlet nipple fitting 61 to be operated on by the sensor assembly. Drain plug 106 seals filter 97, specifically outer chamber 105, regardless of angular orientation of the gas analyzer 10, so that moisture and dirt does not spill into sensor assembly 44 or other circuitry in gas analyzer 10 when gas analyzer 10 is held at an angle. Drain plug 106 is readily removable from its sealed position by a user, so that filter 97 can be drained of moisture and dirt at any time. Filter assembly 40 preferably sits in a recess in the back of the housing of the gas analyzer, so that its parts can be easily accessed.

FIG. 7 is a block diagram showing the logical electrical components of the portable, hand-held gas vehicle gas analyzer 10. Gas analyzer 10 includes keyboards 14a and 14b, display 16, controller PCB 46, sensor assembly 44, filter assembly 40, power port 32, inlet port nipple 19 and outlet port 34. A vehicle 110 under test includes a cigarette lighter receptacle 112 and a tailpipe 114.

Controller PCB 28 includes DC power jack 116, power supply circuit 118, microcontroller 120, one-time programmable read-only memory (OTPROM) 122, flash memory 124, static random access memory (SRAM) 126, DUART 128, realtime clock 130, battery 132, beeper 133, RS-232 transceiver 134, DB9S connector 28, DB9P connector 30, and header/harness 136. Sensor assembly 44 includes sample cell 88, pump assembly 84, NOx sensor 92, $O_2$ sensor 94, and sensor assembly controller 138.

Display 16 may for example be a graphic LCD assembly including a backlight and PCB harnesses. Keyboards 14a and 14b may also include PCB harnesses. Display 16 is communicatively coupled to controller 28. Keyboard 14 is also communicatively coupled to controller 28. Display 16 and keyboard 14 together make up a user interface, allowing a user to input instructions and view results of operations of the gas analyzer.

Power is provided to gas analyzer 10 by either cigarette lighter receptacle 112 in vehicle 110 being tested, or by wall adapter 140. 12-volt DC power is routed through plug 142 to gas analyzer 10 via power port 32. Exhaust gas from vehicle 110 is emitted through tail pipe 114 to sample probe/hose 17, which connects to nipple 19 to enter the gas analyzer. The exhaust then enters filter assembly 40 which operates to filter dirt and condensation from the exhaust. Exhaust then proceeds to sensor assembly 44, and specifically to pump 84. Pump 84 distributes the filtered exhaust to sample cell 88, NOx sensor 92 and $O_2$ sensor 94, for analysis of gas content in the exhaust. The sample rate is preferably less than about one liter per minute, enabling use of a small sample hose such as one-eighth inch inner diameter tubing and a low power pump assembly 84. Sensor assembly 44 is controlled by its controller PCB 138 and its associated circuitry. Sensor assembly controller 138 also operates to communicate with the rest of gas analyzer 10, through header/harness 136.

Main controller PCB 46 operates to regulate operation of the gas analyzer 10. Specifically, DC power jack 116 receives external power through plug 142. The power is delivered to power supply circuit 118, which distributes power throughout the gas analyzer. Power is directly distributed to display 16 as 5V, −24V, adjust and 80V signals, and to sensor assembly 44 as 5V, 12V, −12V and pump 12V signals. Power supply 48 supplies 5-volt and reset signals that are used by the circuitry contained within the controller 46. Power supply 118 delivers 8 watts of total power to the gas analyzer 10 to power its operation. Preferably 6 watts are delivered to sensor assembly 44, and 2 watts are delivered to the remainder of gas analyzer 10.

Microcontroller 120 operates to control the various circuitry elements in the controller 46. Microcontroller 120 may, for example, be a 68331 microprocessor manufactured by Motorola Corporation. Microcontroller 120 delivers control signals and receives input signals from display 16, keyboards 14a and 14b, OTPROM 122, flash 124, SRAM 126 and DUART 128. Realtime clock 130 communicates with microcontroller 120 via the serial peripheral interface (SPI) of microcontroller 120 and provides an automatic time stamp for events recorded by the gas analyzer 10. Battery 132 maintains power to realtime clock 130 when no power is delivered to gas analyzer 10. Beeper 133 is connected to microcontroller 120 and is controlled to sound when certain events demanding a user's attention occur. RS-232 transceiver 134 conditions signals to and from microcontroller 120 via the serial communication interface (SCI) of microcontroller 120. DUART 128 is coupled to microcontroller 120 and to RS-232 transceiver 134, and along with RS-232 transceiver 134 provides an interpreting interface so that microcontroller 120 can communicate in RS-232 format. SRAM 126 is connected to microprocessor 120, and contains temporary memory for program execution to operate the gas analyzer 10. OTPROM 122 contains the boot code that is required for the gas analyzer 10 to power up. Flash memory 124 contains additional application code to be executed in operation of the gas analyzer 10. Memory is divided in this fashion so that static code that does not need to undergo revisions is saved in a static memory such as OTPROM 122, while dynamic code that is periodically revised can be changed by updating flash memory 124. DB9S connector 28 and DB9P connector 30 are provided to allow connection to an external PC or to a printer or modem, respectively. PC bypass line 144 is provided to allow direct communication between sensor assembly 44 and an external PC.

In operation, a user manually couples sample hose/probe 17 to tailpipe 114 of vehicle 110, and inserts the opposite end of sample hose/probe 17 into gas analyzer 10 through nipple 19. Preferably, the user has previously calibrated gas analyzer 10 by connecting to a sample gas canister with known gas content and placing gas analyzer 10 in calibration mode by inputting appropriate instructions via keyboard 14a or 14b. Exhaust from tail pipe 114 travels through sample hose/probe 17 and nipple 19 into filter assembly 40. Filter assembly 40 operates to filter dirt and condensation from the exhaust. The filtered exhaust then travels into sample cell 88, where the content of carbon monoxide, carbon dioxide and hydrocarbons is determined. Pump 84 then advances the exhaust into NOx sensor 92 and $O_2$ sensor 94. Exhaust then exits gas analyzer 10 via nipple fitting 61 through exhaust outlet port 34.

While the exhaust is being tested within sensor assembly 44, controller 46 operates to convert raw data obtained by sensor assembly 44 and interpreted by sensor assembly controller 138 into useful vehicle diagnostic values such as air/fuel ratio (AFR), lambda values, and average mass values. Data from sensor assembly 44 (and specifically from sensor assembly controller 138) is communicated to controller 46 through header/harness 136, and is interpreted by RS-232 transceiver 134. RS-232 transceiver 134 communicates with microcontroller 120 by the serial communication interface (SCI) of microcontroller 120 and through DUART 128 connected to microcontroller 120. Software for converting the data into usable values and for display formatting, etc., resides in flash memory 124 coupled to microcontroller 120. The software includes user interfacing, menus to direct a user in operating the gas analyzer 10, error messages, and the order in which operations occur. The software also preferably includes diagnostic algorithms to direct a repair technician in working on the vehicle under test. Data from sensor assembly 44 interpreted and converted by microprocessor 120 is updated on display 16 four times per second for viewing by a user. The data may be displayed as digital numerals or graphically, for example. Other software necessary for operation of gas analyzer 10 resides in OTPROM 122 and SRAM 126, which are nonvolatile memories. The software in flash memory 124 can be updated directly by downloading via a modem. DB9P connector 30 allows connection to a modem. A user purchasing a product such as gas analyzer 10 may also purchase certificates having a number that allows access to a remote bulletin board system which makes software updates available. Other security measures such as the serial number of the particular gas analyzer 10 may be stored in nonvolatile memory to ensure that software updates are only downloaded to authorized users. Updated software is downloaded by modem through RS-232 transceiver 134 and DUART 128, and operates to re-flash memory 124 to contain the updated software.

The gas analyzer may alternatively operate in a mode utilizing PC bypass 144. In this mode, when an external PC is coupled to gas analyzer 10 via DB9S connector 28, RS-232 transceiver 134 "shuts off" communication with header/harness 136 and sensor assembly 44. Sensor assembly 44 communicates directly with the external PC through header/harness 136 and PC bypass 144. Although sensor assembly 44 does not communicate data with controller 46 in this mode, power is still provided to sensor assembly 44 through header/harness 136 from power supply circuit 118.

Communication between sensor assembly 44 and the external PC through PC bypass 144 is in RS-232 format. Signal conditioning, formatting, and other software operations are performed by the external PC, so that data from sensor assembly 44 can be interpreted and converted into useable values for vehicle diagnostics. Because of the vast memory available for storing and executing software software, and potentially superior display capabilities, it is occasionally desirable to utilize PC bypass 144 to analyze and/or display real-time parameters sensed by sensor assembly 44.

The external PC may also be used in conjunction with the normal operation of gas analyzer 10, wherein sensor assembly 44 is communicating data with controller 46 through header/harness 136 and RS-232 transceiver 134. The external PC may monitor the conditioning of signals from sensor assembly 44, along with other operations of controller 46. In another configuration, controller 46 may store data received from sensor assembly 44 as an event, and download the event data to the external PC in a batch mode, for further analysis by the external PC.

The portable, hand-held vehicle gas analyzer 10 described above is of a size and weight to be easily held in the hands of a user. The gas analyzer preferably weighs less than about five pounds, and preferably has outer dimensions of about 12 inches by 8 inches by 3 inches. The housing of the gas analyzer is preferably composed of a polymeric material, which is possible because the sensor assembly in the gas analyzer operates at ambient temperature. The sensor assembly also does not require a chopper motor, and draws only about 6 watts of total power. Gas analyzer 10 therefore provides full functionality, measuring the content of up to five gases in exhaust emitted from a vehicle under test and displaying the results of its analysis, in a lightweight, hand-held package.

Although the present invention has been described with reference to preferred embodiments, workers skilled in the art will recognize that changes may be made in form and detail without departing from the spirit and scope of the invention.

What is claimed is:

1. A vehicle exhaust analyzing system of a size and weight to be held in a user's hands, the system comprising:

a polymeric housing having outer dimensions no greater than about 12 inches by 8 inches by 3 inches, and having an inlet receiving exhaust emitted from a vehicle under test through a sample hose providing a sealed path for exhaust to travel from the vehicle to the inlet, the sample hose having an inner diameter of about one-eighth of an inch;

a filtering system recessed in the housing, comprising:
      means for receiving the exhaust emitted from the vehicle through the inlet;
      a filter assembly separating gas in the received exhaust from dirt and moisture in the received exhaust;
      a seal disposed on the filter assembly to trap dirt and moisture separated from the received exhaust within the filter assembly, such that dirt and moisture remain within the filter assembly at all angular orientations of the housing until the seal is physically opened; and
      means for passing only the gas separated from the received exhaust out of the filter assembly;

a sensor assembly functioning at ambient temperature, the sensor assembly being disposed in the housing and receiving the filtered exhaust from the filtering system, the sensor assembly comprising:
      a differential infrared sensing system disposed in the housing in a gas flow path operating on the filtered exhaust to determine content of carbon monoxide, carbon dioxide and hydrocarbons in the filtered exhaust;
      a chemical sensing system disposed in the housing in the gas flow path operating on the filtered exhaust to determine content of oxygen and oxides of nitrogen in the filtered exhaust; and
      a pump assembly advancing the filtered exhaust in the gas flow path through the infrared sensing system and the chemical sensing system at a rate of less than about one liter per minute;

a user interface disposed on an outside surface of the housing, including at least one keypad for allowing a user to input instructions while holding the housing and a display for allowing a user to perceive output while holding the housing;

a control system disposed in the housing and operatively coupled with the sensor assembly and the user interface, the control system operable to receive and interpret instructions input by a user via the at least one keypad, regulate operations of the sensor assembly in response to the instructions received, receive and interpret results of operations of the sensor assembly, and transmit the results for display as output on the display;

a power supplying apparatus disposed in the housing, the power supplying apparatus delivering no greater than about 8 watts of power to the sensor assembly, the user interface and the control system; and wherein the housing, the filtering system, the sensor assembly, the user interface, the control system and the power supplying apparatus have a combined weight of no greater than about five pounds.

2. A hand-held vehicle exhaust analyzer comprising:

a housing having an inlet receiving exhaust through a sample hose and probe from a vehicle under test;

a filter assembly receiving the exhaust emitted from the vehicle through the inlet, removing condensation from the exhaust and trapping the condensation within the filter assembly, and outputting filtered exhaust, wherein the filter assembly comprises:
      means for receiving exhaust emitted from the vehicle under test once the exhaust enters the housing through the inlet;
      a filter separating gas in the received exhaust from solid and liquid matter in the received exhaust;
      a removable seal on the filter for trapping solid and liquid matter separated from the received exhaust within the filter, such that the solid and liquid matter remains within the filter at all angular orientations of the housing until the removable seal is physically opened; and
      means for passing only the gas separated from the received exhaust outside the filter;

a sensor assembly functioning at ambient temperature, the sensor assembly being disposed in the housing and comprising:
      a differential infrared sensor disposed in the housing in a gas flow path for measuring a content of carbon monoxide, carbon dioxide and hydrocarbons in the filtered exhaust;
      means disposed in the housing in the gas flow path for measuring a content of oxygen and oxides of nitrogen in the filtered exhaust; and
      a pump assembly advancing the filtered exhaust in the gas flow path through the differential infrared sensor and the means for measuring content of oxygen and oxides of nitrogen;

input means disposed on an outside surface of the housing to allow a user to input instructions while holding the housing;

output means disposed on the outside surface of the housing to allow a user to perceive output while holding the housing;

a control system disposed in the housing and operatively coupled with the sensor assembly, the input means and the output means, the control system receiving and interpreting instructions input by the user via the input means, regulating operations of the sensor assembly in response to the instructions received, receiving and interpreting results of operations of the sensor assembly, and transmitting the results as output to the output means;

a power supply disposed in the housing, the power supply receiving power from a source located externally from the housing and delivering power to the sensor assembly, the input means, the output means and the control system; and wherein the housing, the filter assembly, the sensor assembly, the input means, the output means, the control system and the power supply have a combined weight of no greater than about five pounds.

3. The hand-held vehicle exhaust analyzer of claim 2, wherein the filter comprises:

a manifold having a labyrinth therein to condense liquid from the received exhaust;

an inner chamber;

an outer chamber around the inner chamber;

a first passage between the manifold and the outer chamber for exhaust to proceed from the manifold to the outer chamber;

a hydrophilic filter between the outer chamber and the inner chamber to extract solid and liquid matter from the exhaust received in the outer chamber, so that only filtered exhaust is contained in the inner chamber; and a second passage between the inner chamber and the manifold for filtered exhaust to proceed from the inner chamber to the manifold.

4. The hand-held vehicle exhaust analyzer of claim 3, wherein the removable seal seals the outer chamber.

5. The hand-held vehicle exhaust analyzer of claim 2, wherein the control system includes a PC bypass mechanism for communicating data directly between the sensor assembly and an external computer operatively attachable to the vehicle exhaust analyzing system.

6. The hand-held vehicle exhaust analyzer of claim 2, wherein the housing is composed of a polymeric material.

7. The hand-held vehicle exhaust analyzer of claim 2, wherein the housing has outer dimensions no greater than about 12 inches by 8 inches by 3 inches.

8. The hand-held vehicle exhaust analyzer of claim 2, wherein the power supply delivers no greater than about 8 watts of power to the sensor assembly, the input means, the output means and the control system.

* * * * *